(12) United States Patent
Rao et al.

(10) Patent No.: US 11,376,118 B2
(45) Date of Patent: Jul. 5, 2022

(54) TRACHEA ESOPHAGEAL VOICE PROSTHESIS

(71) Applicants: Vishal Uchila Shishir Rao, Bangalore (IN); Shashank Mahesh, Bangalore (IN)

(72) Inventors: Vishal Uchila Shishir Rao, Bangalore (IN); Shashank Mahesh, Bangalore (IN)

(*) Notice: Subject to any disclaimer, the term of this patent is extended or adjusted under 35 U.S.C. 154(b) by 24 days.

(21) Appl. No.: 16/060,621

(22) PCT Filed: Oct. 19, 2016

(86) PCT No.: PCT/IB2016/056270
§ 371 (c)(1),
(2) Date: Jun. 8, 2018

(87) PCT Pub. No.: WO2017/068503
PCT Pub. Date: Apr. 27, 2017

(65) Prior Publication Data
US 2019/0046313 A1    Feb. 14, 2019

(30) Foreign Application Priority Data
Oct. 19, 2015  (IN) .......................... 5609/CHE/2015

(51) Int. Cl.
*A61F 2/20*   (2006.01)
*A61M 16/04*  (2006.01)
*A61L 27/18*  (2006.01)

(52) U.S. Cl.
CPC .............. *A61F 2/203* (2013.01); *A61L 27/18* (2013.01); *A61M 16/0468* (2013.01);
(Continued)

(58) Field of Classification Search
CPC .............. A61F 2/203; A61F 2220/0025; A61F 2230/0069; A61F 2002/206; A61L 27/18; A61M 16/0468
(Continued)

(56) References Cited

U.S. PATENT DOCUMENTS 3,978,286 A * 8/1976 Watson .................... G10K 9/10
                                                     381/70
4,911,716 A * 3/1990 Blom ...................... A61F 2/203
                                                     128/200.26

(Continued)

OTHER PUBLICATIONS

International Search Report dated Jan. 16, 2017 for corresponding International Application No. PCT/IB2016/056270, filed Oct. 19, 2016.
(Continued)

*Primary Examiner* — Jerrah Edwards
*Assistant Examiner* — Aren Patel
(74) *Attorney, Agent, or Firm* — Westman, Champlin & Koehler, P.A.

(57) ABSTRACT

The disclosure relates to voice prosthesis device that enables a laryngectomy patient to speak. The voice prosthesis device has a cylinder including a first end and a second end. An inner washer is attached to the first end and an outer washer is attached to the second end. A partial shutter is coupled to the first end of the cylinder. A shutter guard is placed at the inner part of the inner washer and is fixed to the cylinder. The device further includes plurality of rings. The partial shutter is made of platinum cured silicon and opens relatively to allow exhaled air to pass from the second end to the first end and prevents entry of food particles into the second end.

11 Claims, 3 Drawing Sheets

(52) U.S. Cl.
CPC .......... *A61F 2220/0025* (2013.01); *A61F 2230/0069* (2013.01); *A61F 2250/007* (2013.01)

(58) Field of Classification Search
USPC .......................................................... 623/9
See application file for complete search history.

(56) References Cited

U.S. PATENT DOCUMENTS

| | | | |
|---|---|---|---|
| 5,433,747 A | 7/1995 | Grundei | |
| 7,025,784 B1 * | 4/2006 | Blom | A61F 2/20 |
| | | | 623/14.11 |
| 7,166,128 B1 | 1/2007 | Persson | |
| 2008/0063585 A1 * | 3/2008 | Smalley | B82Y 40/00 |
| | | | 423/414 |
| 2011/0264214 A1 | 10/2011 | Nelson | |
| 2013/0274876 A1 | 10/2013 | Blom et al. | |
| 2013/0289722 A1 | 10/2013 | Leibitzki et al. | |
| 2013/0304212 A1 * | 11/2013 | VonGunten | A61F 2/442 |
| | | | 623/17.16 |
| 2014/0288648 A1 * | 9/2014 | Walder | A61F 2/203 |
| | | | 623/9 |

OTHER PUBLICATIONS

Written Opinion of the International Searching Authority dated Jan. 16, 2017 for corresponding International Application No. PCT/IB2016/056270, filed Oct. 19, 2016.

* cited by examiner

TRACHEA ESOPHAGEAL VOICE PROSTHESIS

CROSS-REFERENCE TO RELATED APPLICATION

This Application is a Section 371 National Stage Application of International Application No. PCT/IB2016/056270, filed Oct. 19, 2016 and published as WO 2017/068503 A1 on Apr. 27, 2017, in English, the contents of which are hereby incorporated by reference in their entirety.

DESCRIPTION OF THE INVENTION

Technical Field of the Invention

The present invention relates to a voice prosthesis device, which is implanted in the trachea esophageal region that enables laryngectomy patient to speak. The voice prosthesis device includes a cylinder that has a first end and a second end, an outer washer, an inner washer, a partial shutter, a shutter guard and silicon rings.

Background of the Invention

Larynx is the part of the throat, which is located between the base of the tongue and the trachea (wind pipe). The vocal chords in the larynx vibrate and make the sound when the air is passed through, allowing the person to speak. It also plays an important role in breathing.

Laryngeal cancer affects the larynx and is the most common cancer in the head-and-neck region. Laryngeal cancer affects the vocal cords resulting in hoarseness or a change in the voice and ear pain. Recently, the percentage of laryngeal cancer has been increased due to increase in the use of tobacco and alcohol products, nutritional deficiencies, genetic predisposition etc. The symptoms of laryngeal cancer include sore throat, ear pain, cough, change in the voice, pain while swallowing the food etc.

Laryngeal cancer is usually the squamous cell carcinoma originated from the skin of the larynx. The treatment of laryngeal cancer depends on the severity or progression of the disease and stage of diagnosis. Radiotherapy or chemotherapy is recommended at the initial stage. However, severe cancer in the laryngeal or hypopharyngeal region and progression in the disease requires total laryngectomy, i.e. excision of the larynx including vocal folds, which results in loss of speech in the patient.

In order to achieve voice rehabilitation in patients after laryngectomy, artificial implants or prosthesis are inserted during surgery. However, sometimes, these implants, in spite of speech therapy, are not successful in regaining accurate voice due to hypertonicity and hypotonicity. Further, these implants are associated with poor voice quality resulting in difficulty to understand and are not gender-discriminative. In addition, leakage through or around the prosthesis/implant leads to frequent replacements of the prosthesis with an impact on the quality of life of the patient.

The U.S. patent application Ser. No. 13/879,996 titled "Device in the form of a tracheal cannula or a prosthesis for restoring the voice, to be inserted in a tracheostoma" describes a device for insertion into a hole between the trachea and the esophagus in a tracheostoma, which includes a cylindrical body having a longitudinal axis, a flexible flange which is provided on an outer surface of the device body and has unfolded configuration which it extends essentially from the outer surface of the body to the outside and has a folded configuration in which it is folded in the direction towards the longitudinal axis of the device body, as well as a pin-shaped insertion aid having a means for retaining the flange in its bided orientation, wherein the flange is formed by at least two wings each of which have a recess proximate a tip of the wing in which the retaining means is removably introduced and the wings have a shape memory that orients the wings when unrestrained away from the longitudinal axis of the device body. However, the cited document may result in leakage of food after implantation in patient.

The U.S. patent application Ser. No. 13/446,657 titled "Catheter for inserting voice prosthesis" discloses a catheter, voice prosthesis assembly, and delivery method include an elongated flexible body having hollow voice prosthesis tubing disposed on a first end of the elongated flexible body. The voice prosthesis is a one-way valve placed into a puncture between the trachea and the esophagus of a user who cannot speak following total laryngectomy, or surgical removal of the larynx. The voice prosthesis is received in the hollow voice prosthesis tubing. The voice prosthesis having an interior esophageal flange at a first end and an exterior tracheal flange at a second end, whereas the voice prosthesis being received in the hollow voice prosthesis tubing with the interior esophageal flange being folded within the hollow voice prosthesis tubing and the exterior tracheal flange being disposed exterior to the hollow voice prosthesis tubing. However, the cited document may result in leakage of food after implantation in patient The U.S. patent application Ser. No. 08/071,796 titled "Voice Prosthesis" discloses voice prosthesis for use in a shunt between the trachea and the esophagus of a laryngectomized patient. The voice prosthesis comprises a tube-shaped metal part that exhibits an open, funnel-shaped expansion towards the tracheal end and is provided with at least one element within the path of airstream from the trachea to the esophagus, which is allowed to vibrate to produce an audible tone by the air that enters by way of the prosthesis. However, the voice prosthesis remains in situ for only approximately eight weeks. This results in the deposition of fungus and the hence requires cleaning and replacing the prosthesis very frequently, which also incurs additional costs and inconvenience to the patient.

There are different voice prosthesis devices/implants available for voice rehabilitation in patients undergoing laryngectomy. However, the prostheses are associated with leakage of food, which results in fungal infections and reduce the life span of the prosthesis. This requires frequent replacement of the prosthesis in patient. Further, the cost of the available prostheses is high and is not affordable especially in developing countries.

Hence, there is a need for an improved voice prosthesis device, which is noninvasive, immediately usable in a simple and intuitive manner by a person and available at low cost-price.

SUMMARY OF THE INVENTION

The present invention discloses a voice prosthesis device, which is implanted in patients undergoing laryngectomy enabling the patient to speak after surgery. The voice prosthesis device comprises a cylinder that includes a first end and a second end. The device further includes an outer washer, an inner washer, a partial shutter, a shutter guard and silicon rings. The inner washer is attached to the first end of the cylinder and stabilizes the voice prosthesis device at the first end thus preventing an inward movement of the voice prosthesis device into the trachea. The outer washer is attached to the second end of the cylinder. The outer washer is coupled with the second end of the cylinder and stabilizes the voice prosthesis device at the second end to prevent an inward movement of the voice prosthesis into the esophagus. Further, the inner washer is placed diametrically opposite to the outer washer. The thickness of the outer washer diametrically ranges from 40 mm to 45 mm. The first opening of the cylinder accommodates the partial shutter, which is made up of platinum cured silicon material and allows the air to pass through.

The device further includes a shutter guard placed at the inner part of the inner washer further fixed to the cylinder. The presence of shutter guard prevents the food particles from pushing the shutter inwards. The shutter guard is made up of medical grade material. The device further includes plurality of rings, which are added to the first or the second end of the cylinder based on the size of the voice prosthesis required for a trachea-esophageal wall of the patient.

After the insertion of the prosthesis in the patient after laryngectomy, the prosthesis allows the patient to speak even in the absence of larynx. The partial shutter relatively opens when the air is exhaled from the lungs and allows the air to pass through from the second end to the first end of the cylinder. This mechanism also prevents the entry of food particles into the second end, thus preventing fungal infection in the prosthesis and extending the life span of the prosthesis.

The voice prosthesis allows the patient to speak after laryngectomy. The voice prosthesis is simple, non-invasive and cost effective. The presence of rings in the voice prosthesis helps in preventing the piston effect thus increasing the life span of the prosthesis in the patient.

BRIEF DESCRIPTION OF THE DRAWINGS

This invention is illustrated in the accompanying drawings.

DETAILED DESCRIPTION OF THE INVENTION

In order to more clearly and concisely describe and point out the subject matter of the claimed invention, the following definitions are provided for specific terms, which are used in the following written description.

The term "Prosthesis" refers to a device designed to replace a missing part of the body or to make a part of the body work better.

The term "Laryngectomy" refers to removal of the larynx and separation of the airway from the mouth, nose and esophagus.

The present invention relates to a voice prosthesis device, which is implanted in the trachea esophageal region that enables laryngectomy patient to speak. In patients undergoing laryngectomy, the larynx is removed and as a result the trachea and esophagus are separated from each other. An opening, called as tracheo-esophageal puncture, is created between the trachea and esophagus. The prosthesis is implanted into tracheo-esophageal puncture that enables the patient to speak.

The voice prosthesis comprises a cylinder, which further comprises a first end and a second end, an outer washer, an inner washer, a partial shutter, a shutter guard and rings.

Figure 1:
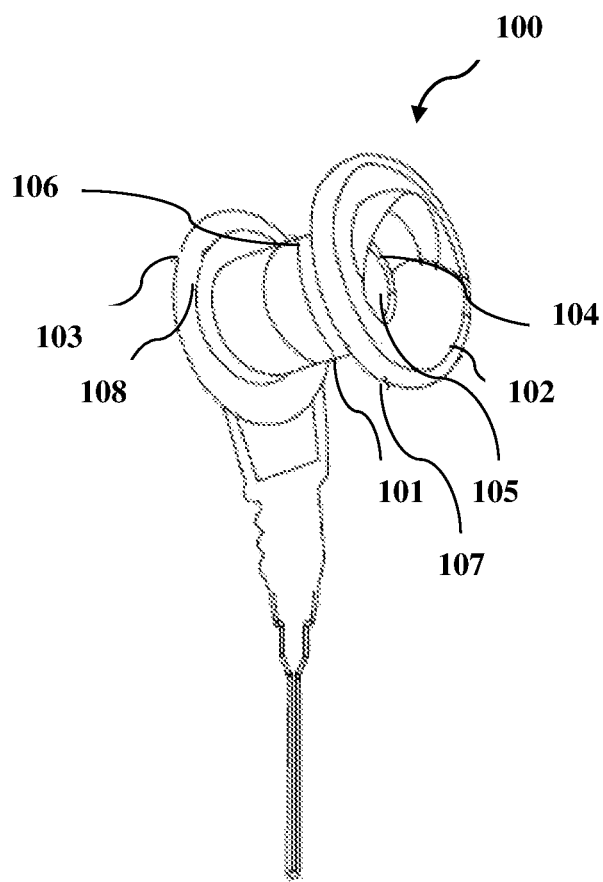
FIG. 1 illustrates the perspective view of the voice prosthesis device.

FIG. 1 illustrates the perspective view of the voice prosthesis device. According to an embodiment of an invention, the voice prosthesis device (100) comprises a cylinder (101), which includes a first end (107) and a second end (108) and an inner washer (102) attached to the first end (107) of the cylinder (101). An outer washer (103) is attached to the second end (108) of the cylinder (101) and a partial shutter (104) is coupled to the first end (107) of the cylinder (101). The device further includes a shutter guard (105) placed at the inner part of the inner washer (102) further fixed to the cylinder (101). The device further includes plurality of rings (106). The first end (107) of the cylinder (101) further comprises a first opening facing towards an esophagus. The first end (107) of the cylinder (101) accommodates the partial shutter (104). The second end (108) of the cylinder (101) further comprises a second opening facing towards a trachea. The inner washer (102) stabilizes the voice prosthesis device (100) at the first end (107) thus preventing an inward movement of the voice prosthesis device (100) into the trachea. The outer washer (103) stabilizes the voice prosthesis device (100) at the second end (108) to prevent an inward movement of the voice prosthesis (100) into the esophagus. Further, the inner washer (102) is placed diametrically opposite to the outer washer (103). The thickness of the outer washer (103) diametrically ranges from 40 mm to 45 mm.

The portion of the partial shutter (104) is coupled to the first end (107) of the cylinder (101). The partial shutter (104) opens relatively and allows the exhaled air to pass from the second end (108) to the first end (107) through the cylinder (101) i.e. from the trachea into the esophagus. Secondly, the partial shutter (104) prevents entry of the food particles into the second end (108) when the air is exhaled from the lungs.

The inner washer (102) accommodates a shutter guard (105). The shutter guard (105) is placed at the inner part of the inner washer (102) and is fixed to the cylinder (101). In a preferred embodiment, the shutter guard (105) is made up of medical grade material. The presence of shutter guard (105) prevents the food particles from pushing the partial shutter (104) inwards and prevents the entry of food particles from the first end (107) into the second end (108).

The voice prosthesis device (100) comprises one or more rings (106), which are added to first end or the second end (108) of the cylinder (101). The rings are circular in shape and are preferably made up of silicon (106). The number of rings (106) varies and depends on the size of the voice prosthesis device (100) required to be placed in the tracheaesophageal puncture of the patient. In most preferable embodiment, the thickness of the rings (106) is 1 mm with a 5 mm aperture at the center. The rings (106) also acts as washer to adapt into the second end (108) in case the size of the voice prosthesis device (100) required for tracheaesophageal puncture is low in a patient. Further, one or more rings (106) are also added as washer to reduce the size of the voice prosthesis device (100). The presence of rings (106) further reduces the piston effect and prevents peri prosthetic leakage of food in patients with thinner partition wall.

Figure 2:
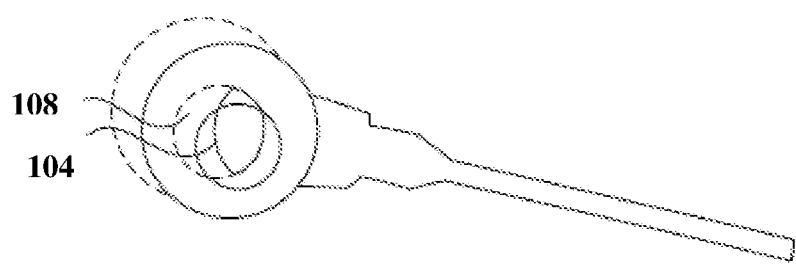
FIG. 2 illustrates the exploded view of the voice prosthesis device.

FIG. 2 illustrates the exploded view of the voice prosthesis device. The portion of the partial shutter (104) is coupled to the first end (107) of the cylinder (101). The partial shutter (104) prevents entry of the food particles into the second end (108) when the air is exhaled from the lungs. The partial shutter (104) is preferably made up of platinum cured silicon material, which exhibits higher tear strength and is more flexible as compared to silicon, which is frequently used in the voice prosthesis device. The thickness of the partial shutter (104) diametrically varies from 3 mm to 7 mm.

Figure 3:
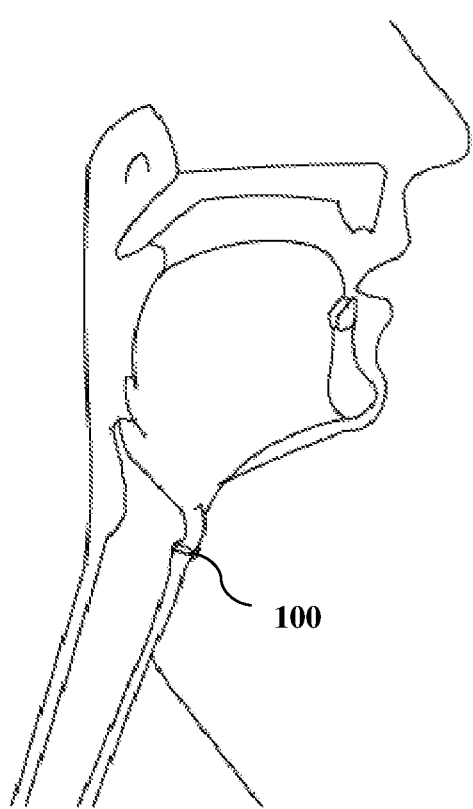
FIG. 3 illustrates the view of the implantation of the voice prosthesis device in a patient after laryngectomy.

FIG. 3 illustrates the view of the implantation of the voice prosthesis device in a patient after laryngectomy. The implantation of the voice prosthesis device (100) into a patient after laryngectomy allows the patient to speak even in the absence of laryx. The partial shutter (104) enables the patient to speak through the voice prosthesis device (100). When the air is inhaled by the patient, the partial shutter (104) is at the open position at the second end (108) and allows the air into the esophagus from the trachea and further allows the air to be delivered from the lungs into the esophagus as it is expelled through the mouth. This passage of the air from the esophagus to the mouth results in the vibration of the tissues in the pharynx thus producing the sound.

The voice prosthesis device is noninvasive, simple and more efficient in producing the voice and is made up of platinum cured silicon, which exhibits high tear strength and is flexible. The addition of silicon rings to the voice prosthesis device prevents the piston effect and peri-prosthetic leakage in patient with thinner tracheo-esophageal puncture. The voice prosthesis device is economical and cost-effective and is affordable especially in developing countries.

We claim:

1. A voice prosthesis device to enable a laryngectomy patient to speak, wherein the voice prosthesis device comprises:
   a. a cylinder comprising a first end and a second end;
   b. an inner washer attached to the first end of the cylinder;
   c. an outer washer attached to the second end of the cylinder;
   d. a partial shutter coupled to the first end of the cylinder;
   e. a shutter guard placed at the inner part of the inner washer, wherein the shutter guard is embedded to the cylinder; and
   f. at least one ring on the cylinder between the inner washer and outer washer.

2. The voice prosthesis device as claimed in claim 1, wherein the inner washer is placed diametrically opposite to the outer washer, wherein:
   the inner washer attached to the first end of the cylinder stabilizes the voice prosthesis device at the first end to preventing an inward movement of the voice prosthesis device into the trachea; and
   the outer washer coupled with the second end of the cylinder stabilizes the voice prosthesis device at the second end to prevent an inward movement of the voice prosthesis into an esophagus.

3. The voice prosthesis device as claimed in claim 1, wherein the partial shutter is made up of platinum cured silicon having an opening between 9 to 3'o clock position and exhibits high tensile strength to prevent food inflow from an esophageal end.

4. The voice prosthesis device as claimed in claim 1, wherein the partial shutter opens partially when the air is exhaled from the lungs to allow the passage of exhaled air from the second end to the first end through the cylinder and in association with shutter guard prevents microbial infection and extends the life span of the voice prosthesis device by avoiding the entry of food particles from the first end into the second end,
   wherein the shutter guard prevents the food particles from pushing the partial shutter inwards.

5. The voice prosthesis device as claimed in claim 1, wherein the voice prosthesis is capable of accommodating multiple rings, and the number of rings to be used depends on the size of the voice prosthesis to be placed in a tracheoesophageal puncture of a patient and the rings are arranged to reduce a piston effect and prevent peri prosthetic leakage of food or fluid.

6. The voice prosthesis device as claimed in claim 1, wherein the partial shutter has a thickness between 3 mm to 7 mm.

7. The voice prosthesis device as claimed in claim 1, wherein the at least one ring comprises at least two rings on the cylinder between the inner washer and the outer washer.

8. A voice prosthesis device to enable a laryngectomy patient to speak, wherein the voice prosthesis device comprises:
   a cylinder comprising a first end and a second end;
   an inner washer attached to the first end of the cylinder;
   an outer washer attached to the second end of the cylinder; and
   at least one ring on the cylinder between the inner washer and outer washer.

9. The voice prosthesis device as claimed in claim 8, wherein the inner washer is placed diametrically opposite to the outer washer, wherein:
   the inner washer attached to the first end of the cylinder stabilizes the voice prosthesis device at the first end to preventing an inward movement of the voice prosthesis device into the trachea; and
   the outer washer coupled with the second end of the cylinder stabilizes the voice prosthesis device at the second end to prevent an inward movement of the voice prosthesis into an esophagus.

10. The voice prosthesis device as claimed in claim 8, wherein the voice prosthesis is capable of accommodating multiple rings, and the number of rings to be used depends on the size of the voice prosthesis to be placed in a tracheoesophageal puncture of a patient and the rings are arranged to reduce a piston effect and prevent peri prosthetic leakage of food or fluid.

11. The voice prosthesis device as claimed in claim 8, wherein the at least one ring comprises at least two rings on the cylinder between the inner washer and the outer washer.

* * * * *